(12) United States Patent
Rhee et al.

(10) Patent No.: US 10,316,074 B2
(45) Date of Patent: Jun. 11, 2019

(54) INTERLEUKIN-2 EXPRESSION CONSTRUCT USING HUMAN SERIUM ALBUMIN

(71) Applicant: SOONCHUNHYANG UNIVERSITY INDUSTRY ACADEMY COOPERATION FOUNDATION, Chungcheongnam-do (KR)

(72) Inventors: Sang-Ki Rhee, Seoul (KR); Eun O Park, Chungcheongnam-do (KR); Hoon Seo, Seoul (KR); Guang Jin Choi, Gyeonggi-do (KR); Keon-Hyoung Song, Chungcheongnam-do (KR)

(73) Assignee: SOONCHUNHYANG UNIVERSITY INDUSTRY ACADEMY COOPERATION FOUNDATION, Chungcheongnam-do (KR)

( * ) Notice: Subject to any disclaimer, the term of this patent is extended or adjusted under 35 U.S.C. 154(b) by 0 days.

(21) Appl. No.: 15/523,288

(22) PCT Filed: May 13, 2015

(86) PCT No.: PCT/KR2015/004787
§ 371 (c)(1),
(2) Date: Apr. 28, 2017

(87) PCT Pub. No.: WO2016/068427
PCT Pub. Date: May 6, 2016

(65) Prior Publication Data
US 2018/0030106 A1 Feb. 1, 2018

(30) Foreign Application Priority Data

Oct. 30, 2014 (KR) .................. 10-2014-0149034
Oct. 30, 2014 (KR) .................. 10-2014-0149042

(51) Int. Cl.
*C07K 14/55* (2006.01)
*C12N 15/81* (2006.01)
*C07K 14/765* (2006.01)
*C12P 21/02* (2006.01)

(52) U.S. Cl.
CPC ............ *C07K 14/55* (2013.01); *C07K 14/765* (2013.01); *C12N 15/81* (2013.01); *C12P 21/02* (2013.01); *C07K 2319/31* (2013.01); *C07K 2319/50* (2013.01)

(58) Field of Classification Search
None
See application file for complete search history.

(56) References Cited

FOREIGN PATENT DOCUMENTS

| KR | 10-2006-0050412 | 5/2006 |
| KR | 10-2006-0131445 | 12/2006 |
| KR | 10-2011-0104348 | 9/2011 |

OTHER PUBLICATIONS

Lei et al. Expression, purification and characterization of recombinant human interleukin-2-serum albumin (rhIL-2-HAS) fusion protein in Pichia pastoris. Protein Expression and Purification. Available online May 17, 2012. vol. 84, pp. 154-160. (Year: 2012).*
Sequence Alignment of SEQ ID No. 3 with SEQ ID No. 2 of U.S. Pat. No. 9,273,116. Search conducted on Mar. 1, 2019, 2 pages. (Year: 2019).*
Kang, H.A. et al., "Development of Expression Systems for the Production of Recombinant Human Serum Albumin Using the MOX Promoter in Hansenula polymorpha DL-1," Biotech. Bioengin. 76:175-185, John Wiley & Sons, Hoboken, NJ (2001).
Melder, R.J. et al., "Pharmacokinetics and In Vitro and In Vivo Anti-Tumor Response of an Interleukin-2-Human Serum Albumin Fusion Protein in Mice," Cancer Immunol. Immunother. 54:535-547, Springer-Verlag GmbH, Berlin, Germany (2005).
Song, H., et al., "Pichia Augusta Hypothetical Protein Gene, Complete CDs; and MOX Gene, Promoter Region," GenBank Assession No. AY550079.1 (2004).
Yu, Z., et al., "*Homo sapiens* Serum Albumin Precursor, mRNA, Complete CDs," GenBank Assession No. AY728024.1 (2004).
English Translation of and International Search Report of PCT/KR2015/004787, WIPO (dated Jul. 8, 2015).
English Translation of and International Search Report of PCT/KR2015/004788, WIPO (dated Aug. 18, 2015).

* cited by examiner

*Primary Examiner* — Channing S Mahatan
(74) *Attorney, Agent, or Firm* — Rubin and Rudman, LLP

(57) ABSTRACT

The present invention relates to an interleukin-2 expression construct for yeast, comprising a methanol oxidase (MOX) promoter; a human serum albumin gene or a fragment thereof; and an interleukin-2 (IL-2) gene, and to a yeast comprising the expression construct. The interleukin-2 expression construct for yeast according to the present invention makes it possible to produce an expressed and secreted fusion protein of human serum albumin (HSA) and interleukin-2 at low costs and easily separate recombinant interleukin-2 from the fusion protein. Thus, the interleukin-2 expression construct for yeast may be effectively used to produce a large amount of recombinant interleukin-2 with high purity.

9 Claims, 4 Drawing Sheets
Specification includes a Sequence Listing.

[Fig. 1]
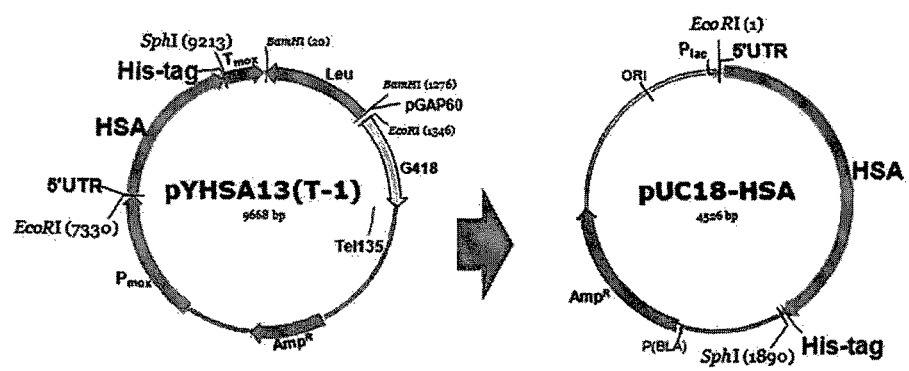
[Fig. 2]
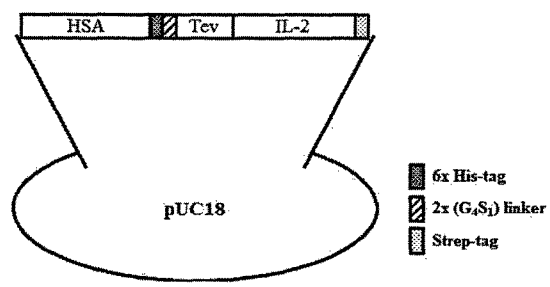

[Fig. 3]
(a)
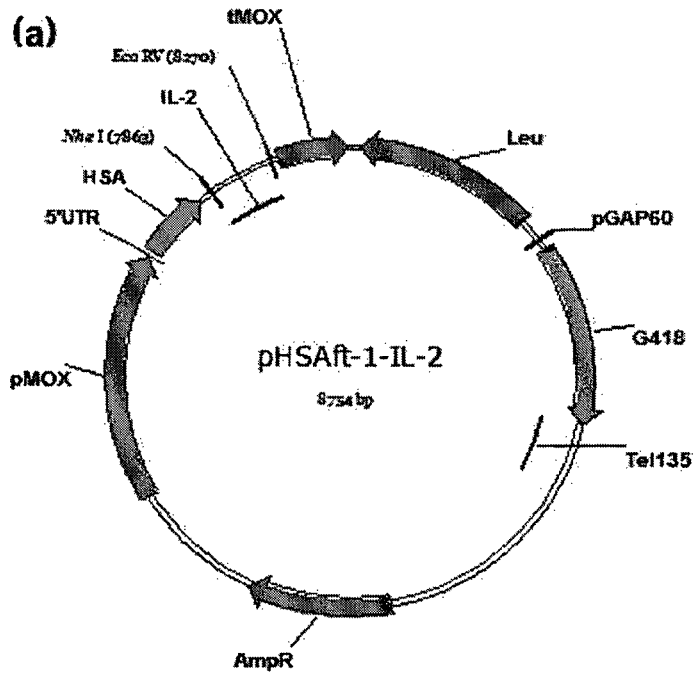
(b)
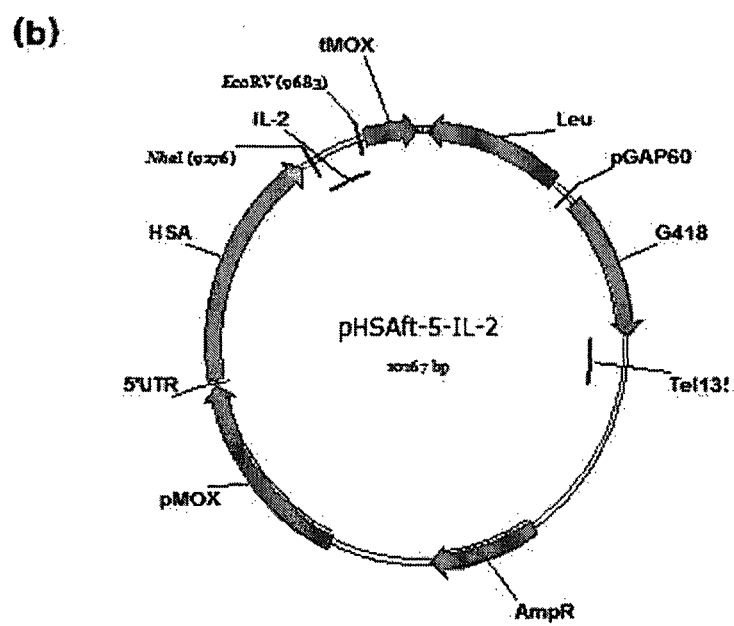

[Fig. 4]
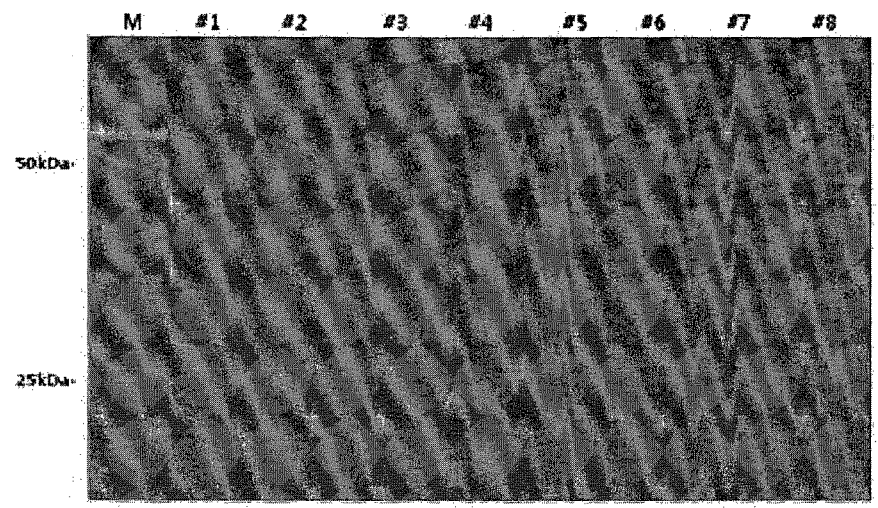
[Fig. 5]
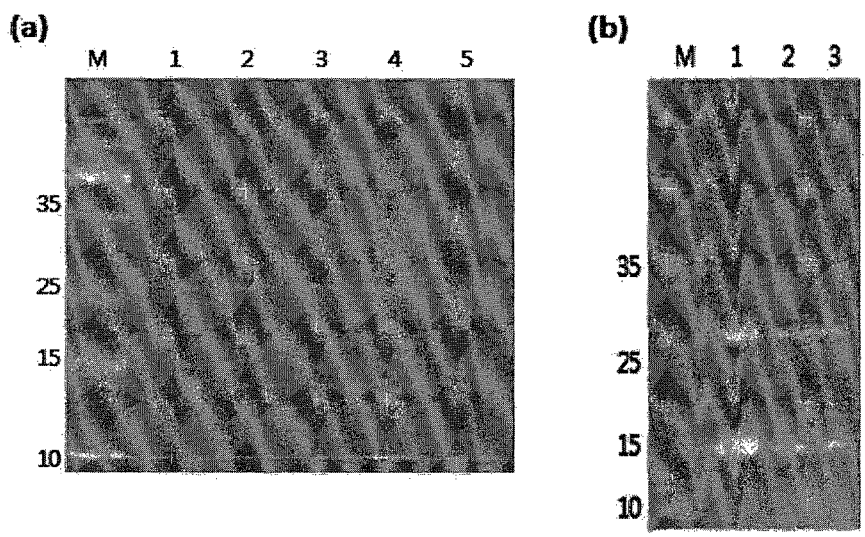

[Fig. 6]
(a)
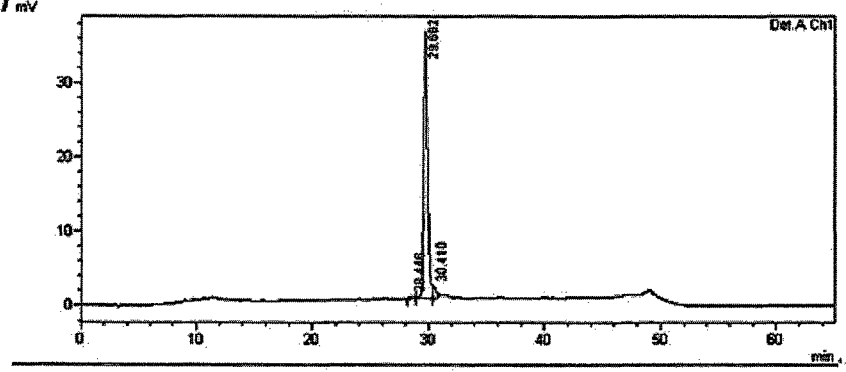
(b)
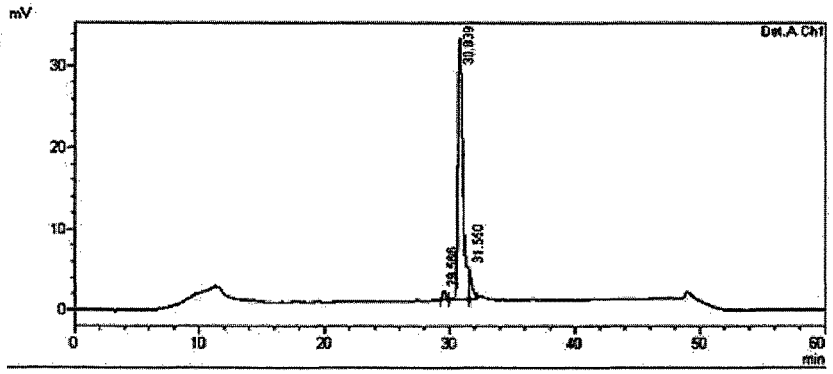

SEQUENCE LISTING

<160> NUMBER OF SEQ ID NOS: 15

<210> SEQ ID NO 1
<211> LENGTH: 1523
<212> TYPE: DNA
<213> ORGANISM: Hansenula polymorpha
<220> FEATURE:
<221> NAME/KEY: promoter
<222> LOCATION: (1)..(1523)
<223> OTHER INFORMATION: Mox promoter

<400> SEQUENCE: 1

```
gcgaagaacg atctcctcga gctgttcgcg gatcagcttg tagccctgca gtggaaccag      60
gccgacggcc cgctccttgc ggaccacggt ggctggcgcg cccaatttgt gaaccaggtc     120
gtttaggacc tcctgcgcaa agtccagtgt taggagaatg tcctcctggg accaattcag     180
catgttctcg agcagccatc tgtctttgga gtaaaaacgt aatttctgct cctcgttact     240
gtaccggaaa agataatttg cctcgccgcc cataataaga aggttctttt tctggtggcc     300
tttgagcagc ggggacgttt ggacagcgtc gatgaggccc ttgaggcgct cgtagtactt     360
ggtcgcgtcg ttgtagccgg ccgcggtgac gatacccaca taaaggtctt tggccattag     420
cttgatgagg tggggtaaga tgggcgactc ggcatcgaaa ttttttgccgt cgtcgtacag     480 tgtgatgtca ccatcgaatg ttatgagctg cagcttgcga tctcggatgg ttttggaatg     540
gaagaaccgc gacatctcca acagctgggc cgtgttgagg atgagccgga cgtcgttgaa     600
cgagggcgcc acaagccggc gtttgctgat ggcgcggcgc tcgtcctcga tgtagaaggc     660
cttttccaga ggcagtctgg tgaaaaagtt gccaacgctc ggaaccagct gcacgagccg     720
agacaattcg ggggtgccgg ctttggtcat ttcaatgttg tcgtcgatga ggagttcgag     780
gtcgtggaag atttctgcgt aacggcgttt tgcctcagag ttcaccatga gatcgtccac     840
ggcggagatg ccgttgctct tcaccgcgta caggacgaac ggcgtggcca acaggccctt     900
tatccactct atgaggccgt ctcgacggtg ttccttgagt gcatactcca ctctgtagcg     960
actagtcatc cggaggctgg gctttctgcg ctgggtgtac taattaattg gtgccgcacc    1020
tgtacggggt accttgcatc cttgcaccgc aactaaaata aacccactcg ctttagcctt    1080
cgcgtaaaac tcgtgaatct ggcaactgag ggggttctgc agccgcaacc aaactttatc    1140
gctttgagga cgcagctgga tggtgtcatg tgaggctctg ttctctggcg tagcctacaa    1200
cgtgactttg cctaagcgga cggccctacc cttagctgcc tgcgcctgct accagaaaat    1260
cactagaaca gcagagggcc gatgtggtaa ttggtgcggt gtcggccagt ctgtttctcc    1320
acagtgcaaa tgcgggtgaa ccggccagaa agcaaatttc ttatgctacc gtgcagtgac    1380
tccgacatcc ccagttttg ccctacttga tcacagatgg ggtcagcact gtcgctaagt    1440
gcacccagtc gtccccacac gcgcaatcta taaatactgc cgccagtgca cggtggtgac    1500
```
atcaatctaa agtacaaaaa caa              1523

<210> SEQ ID NO 2
<211> LENGTH: 1824
<212> TYPE: DNA
<213> ORGANISM: Homo sapiens
<220> FEATURE:
<221> NAME/KEY: gene
<222> LOCATION: (1)..(1824)
<223> OTHER INFORMATION: Human serum albumin

<400> SEQUENCE: 2

| | | | | | |
|---|---|---|---|---|---|
| atgaagtggg | taacctttat | ttcccttctt | tttctcttta | gctcggctta | ttccaggggt | 60 |
| gtgtttcgtc | gagatgcaca | caagagtgag | gttgctcatc | ggtttaaaga | tttgggagaa | 120 |
| gaaaatttca | aagccttggt | gttgattgcc | tttgctcagt | atcttcagca | gtgtccattt | 180 |
| gaagatcatg | taaaattagt | gaatgaagta | actgaatttg | caaaaacatg | tgttgctgat | 240 |
| gagtcagctg | aaaattgtga | caaatcactt | catacccttt | ttggagacaa | attatgcaca | 300 |
| gttgcaactc | ttcgtgaaac | ctatggtgaa | atggctgact | gctgtgcaaa | acaagaacct | 360 |
| gagagaaatg | aatgcttctt | gcaacacaaa | gatgacaatc | caaatctccc | ccgattggtg | 420 |
| agaccagagg | ttgatgtgat | gtgcactgct | tttcatgaca | atgaagagac | attttttgaaa | 480 |
| aaatacttat | atgaaattgc | cagaagacat | ccttactttt | atgccccgga | actccttttc | 540 |
| tttgctaaaa | ggtataaagc | tgcttttaca | gaatgttgcc | aagctgctga | taaagcagcc | 600 |
| tgcctgttgc | caaagctcga | tgaacttcgg | gatgaaggga | aggcttcgtc | tgccaaacag | 660 |
| agactcaagt | gtgccagtct | ccaaaaattt | ggagaaagag | ctttcaaagc | atgggcagta | 720 |
| gctcgcctga | ccagagatt | tcccaaagct | gagtttgcag | aagtttccaa | gttagtgaca | 780 |
| gatcttacca | aagtccacac | ggaatgctgc | catggagatc | tgcttgaatg | tgctgatgac | 840 |
| agggcggacc | ttgccaagta | tatctgtgaa | aatcaagatt | cgatctccag | taaactgaag | 900 |
| gaatgctgtg | aaaaacctct | gttggaaaaa | tcccactgca | ttgccgaagt | ggaaaatgat | 960 |
| gagatgcctg | ctgacttgcc | ttcattagcg | gctgattttg | ttgaaagtaa | ggatgtttgc | 1020 |
| aaaaactatg | ctgaggcaaa | ggatgtcttc | ttgggcatgt | ttttgtatga | atatgcaaga | 1080 |
| aggcatcctg | attactctgt | cgtactgctg | ctgagacttg | ccaagacata | tgaaaccact | 1140 |
| ctagagaagt | gctgtgccgc | tgcagatcct | catgaatgct | atgccaaagt | gttcgatgaa | 1200 |
| tttaaacctc | ttgtggaaga | gcctcagaat | ttaatcaaac | aaaattgtga | gcttttgag | 1260 |
| cagcttggag | agtacaaatt | ccagaatgcg | ctattagttc | gttacaccaa | gaaagtaccc | 1320 |
| caagtgtcaa | ctccaactct | tgtagaggtc | tcaagaaacc | taggaaaagt | gggcagcaaa | 1380 |
| tgttgtaatc | ctgaagcaaa | aagaatgccc | tgtgcagaag | actatctatc | cgtggtcctg | 1440 |
| aaccagttat | gtgtgttgca | tgagaaaacg | ccagtaagtg | acagagtcac | caaatgctgc | 1500 |
| acagaatcct | tggtgaacag | gcgaccatgc | ttttcagctc | tggaagtcga | tgaaacatac | 1560 |
| gttcccaaag | agtttaatgc | tgaaacattc | accttccatg | cagatatatg | cacactttct | 1620 |
| gagaaggaga | gacaaatcaa | gaaacaaact | gcacttgttg | agcttgtgaa | acacaagccc | 1680 |
| aaggcaacaa | aagagcaact | gaaagctgtt | atggatgatt | tcgcagcttt | tgtagagaag | 1740 |
| tgctgcaagg | ctgacgataa | ggaaacctgc | tttgccgagg | agggtaaaaa | acttgttgct | 1800 |
| gcaagtcaag | ctgccttagg | ctta | | | | 1824 |

<210> SEQ ID NO 3

```
<211> LENGTH: 411
<212> TYPE: DNA
<213> ORGANISM: Homo sapiens
<220> FEATURE:
<221> NAME/KEY: gene
<222> LOCATION: (1)..(411)
<223> OTHER INFORMATION: Fragment of human serum albumin

<400> SEQUENCE: 3
atgaagtggg taacctttat ttcccttctt tttctcttta gctcggctta ttccaggggt      60
gtgtttcgtc gagatgcaca caagagtgag gttgctcatc ggtttaaaga tttgggagaa     120
gaaaatttca agccttggt gttgattgcc tttgctcagt atcttcagca gtgtccattt      180
gaagatcatg taaaattagt gaatgaagta actgaatttg caaaaacatg tgttgctgat    240
gagtcagctg aaaattgtga caaatcactt cataccctttt ttggagacaa attatgcaca  300
gttgcaactc ttcgtgaaac ctatggtgaa atggctgact gctgtgcaaa acaagaacct    360
gagagaaatg aatgcttctt gcaacacaaa gatgacaatc caaatctccc c             411

<210> SEQ ID NO 4
<211> LENGTH: 399
<212> TYPE: DNA
<213> ORGANISM: Homo sapiens
<220> FEATURE:
<221> NAME/KEY: gene
<222> LOCATION: (1)..(399)
<223> OTHER INFORMATION: Interleukin-2

<400> SEQUENCE: 4
atgcctactt caagttctac aaagaaaaca cagctacaac tggaacattt actgctggat      60
ttacagatga ttttgaatgg aattaataat acaagaatc ccaaactcac caggatgctc      120
acatttaagt tttacatgcc caagaaggcc acagaattga acatcttca gtgtctagaa      180 gaagaactca aacctctgga ggaagtgcta aatttagctc aaagcaaaaa ctttcactta    240
agacccaggg acttaatcag caatatcaac gtaatagttc tggaactaaa gggatctgaa   300
acaacattca tgtgtgaata tgctgatgag acagcaacca ttgtagaatt tctgaacaga   360
tggattacct tttctcagag catcatctca acactgact                                 399

<210> SEQ ID NO 5
<211> LENGTH: 21
<212> TYPE: DNA
<213> ORGANISM: Artificial Sequence
<220> FEATURE:
<223> OTHER INFORMATION: Tobacco etch virus protease site

<400> SEQUENCE: 5
gaaaacctgt attttcaggg c                                                      21

<210> SEQ ID NO 6
<211> LENGTH: 10167
<212> TYPE: DNA
<213> ORGANISM: Artificial Sequence
<220> FEATURE:
<223> OTHER INFORMATION: pHSAft-5-IL-2 sequence
<220> FEATURE:
<221> NAME/KEY: gene
<222> LOCATION: (7370)..(9193)
<223> OTHER INFORMATION: Human serum Albumin
<220> FEATURE:
<221> NAME/KEY: gene
<222> LOCATION: (9200)..(9223)
<223> OTHER INFORMATION: His tag
<220> FEATURE:
<221> NAME/KEY: gene
```

```
<222> LOCATION: (9224)..(9253)
<223> OTHER INFORMATION: linker
<220> FEATURE:
<221> NAME/KEY: gene
<222> LOCATION: (9254)..(9274)
<223> OTHER INFORMATION: TEV site
<220> FEATURE:
<221> NAME/KEY: gene
<222> LOCATION: (9281)..(9679)
<223> OTHER INFORMATION: Interleukin-2
<220> FEATURE:
<221> NAME/KEY: gene
<222> LOCATION: (9686)..(9709)
<223> OTHER INFORMATION: Strep-tag

<400> SEQUENCE: 6
```

| | | |
|---|---|---|
| gcttatcggg ccgctctagg atcctacttt tttttctccc ttatttagtt cttgagtagc | 60 |
| ttggccacct cctgcgcaac agcatcacca acttcctgtg ttgaggagct tccacccaaa | 120 |
| tcggcagtca tgatacctgc atccaggacg ttcttgacgg cctgctcgat cgcacggccg | 180 |
| gcatccacca agtccagcga cagcttcagc atcatggcgg cagacaaaat tgtggccaat | 240 |
| ggattgacct tgcccgggcc caaatctggc gccgagccgt ggcagggctc gtaaagacca | 300 |
| aacgccttgt ttgtgtctgg cagagacgcc aacgaggcag aaggcagcag gcccagagac | 360 |
| ccaggaatca cactggcctc gtcactgatg atgtcgccaa acatgttgtt ggtgacaatg | 420 |
| acaccgttga gtttcgttgg cgacttgacc aaaatcatgg ctgccgagtc gatcagctgg | 480 |
| tgctgcaccg tcagctgcgg gaactcgttc ttgatggtct cctcaacagt cttccgccac | 540 |
| aaacgcgagg atgcaagcac gttggctttg tccagcgacc acagtgggag cggtgggtcg | 600 |
| ctctgcagcg ccaaaaaggc cgccattctc gtgattctct gcacctctgg aacagaatag | 660 |
| ctctcagtgt cgctggcaac tccgtcgccg gcatcctcct tgcggtcacc aaagtagatt | 720 |
| ccaccaacca actcacgcac aacaacaaag tcagtgccct tgacgatttc tgatttcagt | 780 |
| ggagatagct tcagaagagc gtcggaagca aaactgcatg gacgcaggtt cgcgtacaag | 840 |
| ttgagctctt ttctgatctt caacagaccc tgctcaggac gcacggagcc ggttccccac | 900 |
| ttaggtcctc cgacggctcc aagcaaaacg gcgtcagcct tcttggcggc ttcgagggcc | 960 |
| tcgtcggaca atggcacccc ataagcatcg atcgaggcac cgccgatcag gtgcttggaa | 1020 |
| aagttgaact taacgccgat tgccgacgag acagcctcga gaaccttgac ggcctccgca | 1080 |
| acaacctcgg ggcccacgtg atcaccaggg agaagcacaa tgttcttact catgattgca | 1140 |
| aaatgatgca actatttttgc gccggtaccg ggaaaaattg aaaaaccatc cacttactca | 1200 |
| ttcctgtctt tttatttcgt attaccaaac cgcttacgta ctcacccact cagatcccccc | 1260 |
| gggctgcagg aattggatcc gaccagtctc tctcgcacat tatcaattgc tctttagtac | 1320 |
| aaagataata tagaaacaat attcgaatta attcgttatg agccatattc aacgggaaac | 1380 |
| gtcttgctcg aggccgcgat taaattccaa catggatgct gatttatatg ggtataaatg | 1440 |
| ggctcgcgat aatgtcgggc aatcaggtgc gacaatctat cgattgtatg ggaagcccga | 1500 |
| tgcgccagag ttgtttctga acatggcaa aggtagcgtt gccaatgatg ttacagatga | 1560 |
| gatggtcaga ctaaactggc tgacggaatt tatgcctctt ccgaccatca agcatttat | 1620 |
| ccgtactcct gatgatgcat ggttactcac cactgcgatc cccgggaaaa cagcattcca | 1680 |
| ggtattagaa gaatatcctg attcaggtga aaatattgtt gatgcgctgg cagtgttcct | 1740 |
| gcgccggttg cattcgattc ctgtttgtaa ttgtcctttt aacagcgatc gcgtatttcg | 1800 |
| tctcgctcag gcgcaatcac gaatgaataa cggtttggtt gatgcgagtg attttgatga | 1860 |

```
cgagcgtaat ggctggcctg ttgaacaagt ctggaaagaa atgcataagc tttttgccatt      1920
ctcaccggat tcagtcgtca ctcatggtga tttctcactt gataaccttg tttttgacga       1980
ggggaaatta ataggttgta ttgatgttgg acgagtcgga atcgcagacc gataccagga       2040
tcttgccatc ctatggaact gcctcggtga gttttctcct tcattacaga aacggctttt       2100
tcaaaaatat ggtattgata atcctgatat gaataaattg cagtttcatt tgatgctcga      2160
tgagttttc taatcagaat tggttaattg gttgtaacac tggcagagca ttacgctgac       2220
ttgacgggac ggcggctttg ttgaataaat cgaacttttg ctgagttgaa ggatcagatc      2280
acgcatcttc ccgacaacgc agaccgttcc gtggcaaagc aaaagttcaa atcaccaac       2340
tggtccacct acaacaaagc tctcatcaac cgtggctccc tcactttctg gctggatgat      2400
ggggcgattc aggcctggta tgagtcagca cacccttctt cacgaggcag acctcagcgc      2460
cccccccct gcagtcgaca ggccaacgtg gttgtggcgg agtcggtggt gtttagagag       2520
gaattagagc aagtagaagt atagaaggaa taagccaagt agagacaagt ttaatatatg      2580
tagattaata aggtgagga attagatggg gaggaagcgg caggaagcgg tgtagggatg       2640
cggcgaggaa agcagaggca gctggtttca ggacgcggtc tgaggcctgg ggtggcgggg      2700
tggcggggtg gcggggtggc ggggtggcgg ggtggcgggg tggcggggtg gcggggtggc      2760
ggggtggcgg ggtggcgggg tggcggggtg gcggggtggc ggggtggcgg ggtggcgggg      2820
tggcggggtg gcggggtggc ggggtggcgg ggtggcgggg tggcggggtg gcgatcaagc      2880
ttatcgatac cgtcgacctc gagggggggc ccggtaccca gcttttgttc cctttagtga      2940
gggttaattg cgcgcttggc gtaatcatgg tcatagctgt ttcctgtgtg aaattgttat      3000
ccgctcacaa ttccacacaa catacgagcc ggaagcataa agtgtaaagc ctggggtgcc      3060
taatgagtga gctaactcac attaattgcg ttgcgctcac tgcccgcttt ccagtcggga      3120
aacctgtcgt gccagctgca ttaatgaatc ggccaacgcg cggggagagg cggtttgcgt      3180
attgggcgct cttccgcttc ctcgctcact gactcgctgc gctcggtcgt tcggctgcgg      3240
cgagcggtat cagctcactc aaaggcggta atacggttat ccacagaatc aggggataac      3300
gcaggaaaga acatgtgagc aaaaggccag caaaaggcca ggaaccgtaa aaaggccgcg      3360
ttgctggcgt ttttccatag gctccgcccc cctgacgagc atcacaaaaa tcgacgctca      3420
agtcagaggt ggcgaaaccc gacaggacta taaagatacc aggcgtttcc ccctggaagc      3480
tccctcgtgc gctctcctgt tccgaccctg ccgcttaccg gatacctgtc cgcctttctc      3540
ccttcgggaa gcgtggcgct ttctcatagc tcacgctgta ggtatctcag ttcggtgtag      3600
gtcgttcgct ccaagctggg ctgtgtgcac gaaccccccg ttcagcccga ccgctgcgcc      3660
ttatccggta actatcgtct tgagtccaac ccggtaagac acgacttatc gccactggca      3720
gcagccactg gtaacaggat tagcagagcg aggtatgtag gcggtgctac agagttcttg      3780
aagtggtggc ctaactacgg ctacactaga aggacagtat ttggtatctg cgctctgctg      3840
aagccagtta ccttcggaaa aagagttggt agctcttgat ccggcaaaca aaccaccgct      3900
ggtagcggtg gtttttttgt ttgcaagcag cagattacgc gcagaaaaaa aggatctcaa      3960
gaagatcctt tgatcttttc tacggggtct gacgctcagt ggaacgaaaa ctcacgttaa      4020
gggattttgg tcatgagatt atcaaaaagg atcttcacct agatcctttt aaattaaaaa      4080
tgaagtttta aatcaatcta agtatatatg agtaaacttg gtctgacagt taccaatgc       4140
ttaatcagtg aggcacctat ctcagcgatc tgtctatttc gttcatccat agttgcctga      4200
ctccccgtcg tgtagataac tacgatacgg gagggcttac catctggccc cagtgctgca      4260
```

| | |
|---|---|
| atgataccgc gagacccacg ctcaccggct ccagatttat cagcaataaa ccagccagcc | 4320 |
| ggaagggccg agcgcagaag tggtcctgca actttatccg cctccatcca gtctattaat | 4380 |
| tgttgccggg aagctagagt aagtagttcg ccagttaata gtttgcgcaa cgttgttgcc | 4440 |
| attgctacag gcatcgtggt gtcacgctcg tcgtttggta tggcttcatt cagctccggt | 4500 |
| tcccaacgat caaggcgagt tacatgatcc cccatgttgt gcaaaaaagc ggttagctcc | 4560 |
| ttcggtcctc cgatcgttgt cagaagtaag ttggccgcag tgttatcact catggttatg | 4620 |
| gcagcactgc ataattctct tactgtcatg ccatccgtaa gatgcttttc tgtgactggt | 4680 |
| gagtactcaa ccaagtcatt ctgagaatag tgtatgcggc gaccgagttg ctcttgcccg | 4740 |
| gcgtcaatac gggataatac cgcgccacat agcagaactt taaaagtgct catcattgga | 4800 |
| aaacgttctt cggggcgaaa actctcaagg atcttaccgc tgttgagatc cagttcgatg | 4860 |
| taacccactc gtgcacccaa ctgatcttca gcatctttta ctttcaccag cgtttctggg | 4920 |
| tgagcaaaaa caggaaggca aaatgccgca aaaaagggaa taaggcgac acggaaatgt | 4980 |
| tgaatactca tactcttcct ttttcaatat tattgaagca tttatcaggg ttattgtctc | 5040 |
| atgagcggat acatatttga atgtatttag aaaaataaac aaataggggt tccgcgcaca | 5100 |
| tttccccgaa aagtgccacc taaattgtaa gcgttaatat tttgttaaaa ttcgcgttaa | 5160 |
| attttgtta aatcagctca ttttttaacc aataggccga atcggcaaa atcccttata | 5220 |
| aatcaaaaga atagaccgag atagggttga gtgttgttcc agtttggaac aagagtccac | 5280 |
| tattaaagaa cgtggactcc aacgtcaaag ggcgaaaaac cgtctatcag ggcgatggcc | 5340 |
| cactacgtga accatcaccc taatcaagtt ttttggggtc gaggtgccgt aaagcactaa | 5400 |
| atcggaaccc taaagggagc ccccgattta gagcttgacg gggaaagccg gcgaacgtgg | 5460 |
| cgagaaagga agggaagaaa gcgaaaggag cgggcgctag gcgctggca agtgtagcgg | 5520 |
| tcacgctgcg cgtaaccacc acacccgccg cgcttaatgc gccgctacag ggcgcgtccc | 5580 |
| attcgccatt caggctgcgc aactgttggg aagggcgatc ggtgcgggcc tcttcgctat | 5640 |
| tacgccagct ggcgaaaggg ggatgtgctg caaggcgatt aagttgggta acgccagggt | 5700 |
| tttcccagtc acgacgttgt aaaacgacg ccagtgagcg cgcgtaatac gactcactat | 5760 |
| agggcgaatt ggagctccac cgcggtggcg gccgtcgatc gacgcgaaga acgatctcct | 5820 |
| cgagctgttc gcggatcagc ttgtagccct gcagtggaac caggccgacg gcccgctcct | 5880 |
| tgcggaccac ggtggctggc gcgcccaatt tgtgaaccag gtcgtttagg acctcctgcg | 5940 |
| caaagtccag tgttaggaga atgtcctcct gggaccaatt cagcatgttc tcgagcagcc | 6000 |
| atctgtcttt ggagtaaaaa cgtaatttct gctcctcgtt actgtaccgg aaaagataat | 6060 |
| ttgcctcgcc gccataata agaaggtct ttttctggtg gcctttgagc agcggggacg | 6120 |
| tttggacagc gtcgatgagg cccttgaggc gctcgtagta cttggtcgcg tcgttgtagc | 6180 |
| cggccgcgt gacgataccc acataaaggt ctttggccat tagcttgatg aggtggggta | 6240 |
| agatgggcga ctcggcatcg aaattttgc cgtcgtcgta cagtgtgatg tcaccatcga | 6300 |
| atgttatgag ctgcagcttg cgatctcgga tggttttgga atggaagaac cgcgacatct | 6360 |
| ccaacagctg ggccgtgttg aggatgagcc ggacgtcgtt gaacgagggc gccacaagcc | 6420 |
| ggcgtttgct gatggcgcgg cgctcgtcct cgatgtagaa ggccttttcc agaggcagtc | 6480 |
| tggtgaaaaa gttgccaacg ctcggaacca gctgcacgag ccgagacaat tcggggtgc | 6540 |
| cggctttggt catttcaatg ttgtcgtcga tgaggagttc gaggtcgtgg aagatttctg | 6600 |

```
cgtaacggcg ttttgcctca gagttcacca tgagatcgtc cacggcggag atgccgttgc    6660
tcttcaccgc gtacaggacg aacggcgtgg ccaacaggcc ctttatccac tctatgaggc    6720
cgtctcgacg gtgttccttg agtgcatact ccactctgta gcgactagtc atccggaggc    6780
tgggctttct gcgctgggtg tactaattaa ttggtgccgc acctgtacgg ggtaccttgc    6840
atccttgcac cgcaactaaa ataaacccac tcgctttagc cttcgcgtaa aactcgtgaa    6900
tctggcaact gaggggttc tgcagccgca accaaacttt atcgctttga ggacgcagct    6960
ggatggtgtc atgtgaggct ctgttctctg gcgtagccta caacgtgact ttgcctaagc    7020
ggacggccct acccttagct gcctgcgcct gctaccagaa aatcactaga acagcagagg    7080
gccgatgtgg taattggtgc ggtgtcggcc agtctgtttc tccacagtgc aaatgcgggt    7140
gaaccggcca gaaagcaaat ttcttatgct accgtgcagt gactccgaca tccccagttt    7200
ttgccctact tgatcacaga tggggtcagc actgtcgcta agtgcaccca gtcgtcccca    7260
cacgcgcaat ctataaatac tgccgccagt gcacggtggt gacatcaatc taaagtacaa    7320
aaacaaaagc ttgaattcgg cacgaggtca accccacgcc tttggcacaa tgaagtgggt    7380
aacctttatt tccctctctt ttctcttag ctcggcttat tccagggggtg tgtttcgtcg    7440 agatgcacac aagagtgagg ttgctcatcg gtttaaagat tgggagaag aaaattcaa    7500 agccttggtg ttgattgcct ttgctcagta tcttcagcag tgtccatttg aagatcatgt    7560
aaaattagtg aatgaagtaa ctgaatttgc aaaaacatgt gttgctgatg agtcagctga    7620
aaattgtgac aaatcacttc ataccctttt tggagacaaa ttatgcacag ttgcaactct    7680
tcgtgaaacc tatggtgaaa tggctgactg ctgtgcaaaa caagaacctg agagaaatga    7740
atgcttcttg caacacaaag atgacaatcc aaatctcccc cgattggtga ccagaggt    7800 tgatgtgatg tgcactgctt ttcatgacaa tgaagagaca ttttttgaaaa aatacttata    7860 tgaaattgcc agaagacatc cttactttta tgccccggaa ctccttttct ttgctaaaag    7920
gtataaagct gcttttacag aatgttgcca agctgctgat aaagcagcct gcctgttgcc    7980
aaagctcgat gaacttcggg atgaagggaa ggcttcgtct gccaaacaga gactcaagtg    8040
tgccagtctc caaaaatttg gagaaagagc tttcaaagca tgggcagtag ctcgcctgag    8100
ccagagattt cccaaagctg agtttgcaga agtttccaag ttagtgacag atcttaccaa    8160
agtccacacg gaatgctgcc atggagatct gcttgaatgt gctgatgaca gggcggacct    8220
tgccaagtat atctgtgaaa atcaagattc gatctccagt aaactgaagg aatgctgtga    8280
aaaacctctg ttggaaaaat cccactgcat tgccgaagtg aaaatgatg agatgcctgc    8340 tgacttgcct tcattagcgg ctgattttgt tgaaagtaag gatgtttgca aaaactatgc    8400
tgaggcaaag gatgtcttct tgggcatgtt tttgtatgaa tatgcaagaa ggcatcctga    8460
ttactctgtc gtactgctgc tgagacttgc caagacatat gaaaccactc tagagaagtg    8520
ctgtgccgct gcagatcctc atgaatgcta tgccaaagtg ttcgatgaat ttaaacctct    8580
tgtggaagag cctcagaatt taatcaaaca aaattgtgag cttttttgagc agcttggaga    8640 gtacaaattc cagaatgcgc tattagttcg ttacaccaag aaagtacccc aagtgtcaac    8700
tccaactctt gtagaggtct caagaaacct aggaaaagtg ggcagcaaat gttgtaatcc    8760
tgaagcaaaa agaatgccct gtgcagaaga ctatctatcc gtggtcctga accagttatg    8820
tgtgttgcat gagaaaacgc cagtaagtga cagagtcacc aaatgctgca cagaatcctt    8880
ggtgaacagg cgaccatgct tttcagctct ggaagtcgat gaaacatacg ttcccaaaga    8940
gtttaatgct gaaacattca ccttccatgc agatatatgc acactttctg agaaggagag    9000
```

-continued

| | |
|---|---|
| acaaatcaag aaacaaactg cacttgttga gcttgtgaaa cacaagccca aggcaacaaa | 9060 |
| agagcaactg aaagctgtta tggatgattt cgcagctttt gtagagaagt gctgcaaggc | 9120 |
| tgacgataag gaaacctgct ttgccgagga gggtaaaaaa cttgttgctg caagtcaagc | 9180 |
| tgccttaggc ttagttaacc atcaccatca ccatcaccat cacggtggcg gtggctcggg | 9240 |
| tggcggtgga tccgaaaacc tgtattttca gggcgctagc atgcctactt caagttctac | 9300 |
| aaagaaaaca cagctacaac tggaacattt actgctggat ttacagatga ttttgaatgg | 9360 |
| aattaataat tacaagaatc ccaaactcac caggatgctc acatttaagt tttacatgcc | 9420 |
| caagaaggcc acagaattga aacatcttca gtgtctagaa gaagaactca aacctctgga | 9480 |
| ggaagtgcta aatttagctc aaagcaaaaa ctttcactta agacccaggg acttaatcag | 9540 |
| caatatcaac gtaatagttc tggaactaaa gggatctgaa acaacattca tgtgtgaata | 9600 |
| tgctgatgag acagcaacca ttgtagaatt tctgaacaga tggattaccc tttctcagag | 9660 |
| catcatctca acactgactg atatctggag ccacccgcag ttcgaaaagt gacccatcgc | 9720 |
| tagaactagt ggatcttggc tactcaggct ccgacctgga catgacgatt ccaaacttca | 9780 |
| gactcggaac ttacgaggag accggacttg ccagattcta aggagacgtg aaggacata | 9840 |
| ccgcttttga gaagcgtgtt tgaaaatagt tcttttctg gtttatatcg tttatgaagt | 9900 |
| gatgagatga aagctgaaa tagcgagtat aggaaaattt aatgaaaatt aaattaaata | 9960 |
| ttttcttagg ctattagtca ccttcaaaat gccggccgct tctaagaacg ttgtcatgat | 10020 |
| cgacaactac gactcgtta cctggaacct gtacgagtac ctgtgtcagg agggagccaa | 10080 |
| tgtcgaggtt ttcaggaacg atcagatcac cattccggag attgagcagc tcaagccgga | 10140 |
| cgttgtggtg atgggctgca ggaatta | 10167 |

<210> SEQ ID NO 7
<211> LENGTH: 8754
<212> TYPE: DNA
<213> ORGANISM: Artificial Sequence
<220> FEATURE:
<223> OTHER INFORMATION: pHSAft-1-IL-2 sequence
<220> FEATURE:
<221> NAME/KEY: gene
<222> LOCATION: (7370)..(7780)
<223> OTHER INFORMATION: Human serum albumin
<220> FEATURE:
<221> NAME/KEY: gene
<222> LOCATION: (7787)..(7810)
<223> OTHER INFORMATION: His tag
<220> FEATURE:
<221> NAME/KEY: gene
<222> LOCATION: (7811)..(7840)
<223> OTHER INFORMATION: Linker
<220> FEATURE:
<221> NAME/KEY: gene
<222> LOCATION: (7841)..(7861)
<223> OTHER INFORMATION: TEV site
<220> FEATURE:
<221> NAME/KEY: gene
<222> LOCATION: (7868)..(8266)
<223> OTHER INFORMATION: Interleukin-2
<220> FEATURE:
<221> NAME/KEY: gene
<222> LOCATION: (8273)..(8296)
<223> OTHER INFORMATION: Strep-tag

<400> SEQUENCE: 7

| | |
|---|---|
| gcttatcggg ccgctctagg atcctacttt tttttctccc ttatttagtt cttgagtagc | 60 |
| ttggccacct cctgcgcaac agcatcacca acttcctgtg ttgaggagct tccacccaaa | 120 |

```
tcggcagtca tgatacctgc atccaggacg ttcttgacgg cctgctcgat cgcacggccg    180
gcatccacca agtccagcga cagcttcagc atcatggcgg cagacaaaat tgtggccaat    240
ggattgacct tgcccgggcc caaatctggc gccgagccgt ggcagggctc gtaaagacca    300
aacgccttgt ttgtgtctgg cagagacgcc aacgaggcag aaggcagcag gcccagagac    360
ccaggaatca cactggcctc gtcactgatg atgtcgccaa acatgttgtt ggtgacaatg    420
acaccgttga gtttcgttgg cgacttgacc aaaatcatgg ctgccgagtc gatcagctgg    480
tgctgcaccg tcagctgcgg gaactcgttc ttgatggtct cctcaacagt cttccgccac    540
aaacgcgagg atgcaagcac gttggctttg tccagcgacc acagtgggag cggtgggtcg    600
ctctgcagcg ccaaaaaggc cgccattctc gtgattctct gcacctctgg aacagaatag    660
ctctcagtgt cgctggcaac tccgtcgccg gcatcctcct tgcggtcacc aaagtagatt    720
ccaccaacca actcacgcac aacaacaaag tcagtgccct tgacgatttc tgatttcagt    780
ggagatagct tcagaagagc gtcggaagca aaactgcatg gacgcaggtt cgcgtacaag    840
ttgagctctt ttctgatctt caacagaccc tgctcaggac gcacggagcc ggttccccac    900
ttaggtcctc cgacggctcc aagcaaaacg gcgtcagcct tcttggcggc ttcgagggcc    960
tcgtcggaca atggcacccc ataagcatcg atcgaggcac cgccgatcag gtgcttggaa   1020
aagttgaact taacgccgat tgccgacgag acagcctcga gaaccttgac ggcctccgca   1080
acaacctcgg ggcccacgtg atcaccaggg agaagcacaa tgttcttact catgattgca   1140
aaatgatgca actattttgc gccggtaccg ggaaaaattg aaaaaccatc cacttactca   1200
ttcctgtctt tttatttcgt attaccaaac cgcttacgta ctcacccact cagatccccc   1260
gggctgcagg aattggatcc gaccagtctc tctcgcacat tatcaattgc tctttagtac   1320
aaagataata tagaaacaat attcgaatta attcgttatg agccatattc aacgggaaac   1380
gtcttgctcg aggccgcgat taaattccaa catggatgct gatttatatg ggtataaatg   1440
ggctcgcgat aatgtcgggc aatcaggtgc gacaatctat cgattgtatg ggaagcccga   1500
tgcgccagag ttgtttctga acatggcaa aggtagcgtt gccaatgatg ttacagatga   1560
gatggtcaga ctaaactggc tgacggaatt tatgcctctt ccgaccatca agcattttat   1620
ccgtactcct gatgatgcat ggttactcac cactgcgatc cccgggaaaa cagcattcca   1680
ggtattagaa gaatatcctg attcaggtga aaatattgtt gatgcgctgg cagtgttcct   1740
gcgccggttg cattcgattc ctgtttgtaa ttgtcctttt aacagcgatc gcgtatttcg   1800
tctcgctcag gcgcaatcac gaatgaataa cggtttggtt gatgcgagtg attttgatga   1860
cgagcgtaat ggctggcctg ttgaacaagt ctggaaagaa atgcataagc ttttgccatt   1920
ctcaccggat tcagtcgtca ctcatggtga tttctcactt gataaccttaa ttttgacga   1980 ggggaaatta ataggttgta ttgatgttgg acgagtcgga atcgcagacc gataccagga   2040
tcttgccatc ctatggaact gcctcggtga gttttctcct tcattacaga aacggctttt   2100
tcaaaaatat ggtattgata atcctgatat gaataaattg cagtttcatt tgatgctcga   2160 tgagttttc taatcagaat tggttaattg gttgtaacac tggcagagca ttacgctgac   2220
ttgacgggac ggcggctttg ttgaataaat cgaacttttg ctgagttgaa ggatcagatc   2280
acgcatcttc ccgacaacgc agaccgttcc gtggcaaagc aaaagttcaa aatcaccaac   2340
tggtccacct acaacaaagc tctcatcaac cgtggctccc tcactttctg gctggatgat   2400
ggggcgattc aggcctggta tgagtcagca acaccttctt cacgaggcag acctcagcgc   2460 cccccccct gcagtcgaca ggccaacgtg ttgtggcgg agtcggtggt gtttagagag   2520
```

```
gaattagagc aagtagaagt atagaaggaa taagccaagt agagacaagt ttaatatatg    2580
tagattaata aaggtgagga attagatggg gaggaagcgg caggaagcgg tgtagggatg    2640
cggcgaggaa agcagaggca gctggtttca ggacgcggtc tgaggcctgg ggtggcgggg    2700
tggcggggtg gcggggtggc ggggtggcgg ggtggcgggg tggcggggtg gcggggtggc    2760
ggggtggcgg ggtggcgggg tggcggggtg gcggggtggc ggggtggcgg ggtggcgggg    2820
tggcggggtg gcggggtggc ggggtggcgg ggtggcgggg tggcggggtg gcgatcaagc    2880
ttatcgatac cgtcgacctc gagggggggc ccggtaccca gcttttgttc cctttagtga    2940
gggttaattg cgcgcttggc gtaatcatgg tcatagctgt ttcctgtgtg aaattgttat    3000
ccgctcacaa ttccacacaa catacgagcc ggaagcataa agtgtaaagc ctggggtgcc    3060
taatgagtga gctaactcac attaattgcg ttgcgctcac tgcccgcttt ccagtcggga    3120
aacctgtcgt gccagctgca ttaatgaatc ggccaacgcg cggggagagg cggtttgcgt    3180
attgggcgct cttccgcttc ctcgctcact gactcgctgc gctcggtcgt tcggctgcgg    3240
cgagcggtat cagctcactc aaaggcggta atacggttat ccacagaatc aggggataac    3300
gcaggaaaga acatgtgagc aaaaggccag caaaaggcca ggaaccgtaa aaaggccgcg    3360
ttgctggcgt ttttccatag gctccgcccc cctgacgagc atcacaaaaa tcgacgctca    3420
agtcagaggt ggcgaaaccc gacaggacta taaagatacc aggcgtttcc ccctggaagc    3480
tccctcgtgc gctctcctgt tccgaccctg ccgcttaccg gatacctgtc gcctttctc    3540 ccttcgggaa gcgtggcgct ttctcatagc tcacgctgta ggtatctcag ttcggtgtag    3600
gtcgttcgct ccaagctggg ctgtgtgcac gaaccccccg ttcagcccga ccgctgcgcc    3660
ttatccggta actatcgtct tgagtccaac ccggtaagac acgacttatc gccactggca    3720
gcagccactg gtaacaggat tagcagagcg aggtatgtag gcggtgctac agagttcttg    3780
aagtggtggc ctaactacgg ctacactaga aggacagtat ttggtatctg cgctctgctg    3840
aagccagtta ccttcggaaa aagagttggt agctcttgat ccggcaaaca aaccaccgct    3900
ggtagcggtg ttttttttgt ttgcaagcag cagattacgc gcagaaaaaa aggatctcaa    3960
gaagatcctt tgatcttttc tacggggtct gacgctcagt ggaacgaaaa ctcacgttaa    4020
gggattttgg tcatgagatt atcaaaaagg atcttcacct agatcctttt aaattaaaaa    4080
tgaagtttta aatcaatcta agtatatat gagtaaactt ggtctgacag ttaccaatgc    4140
ttaatcagtg aggcacctat ctcagcgatc tgtctatttc gttcatccat agttgcctga    4200
ctccccgtcg tgtagataac tacgatacgg gagggcttac catctggccc cagtgctgca    4260
atgataccgc gagacccacg ctcaccggct ccagatttat cagcaataaa ccagccagcc    4320
ggaagggccg agcgcagaag tggtcctgca actttatccg cctccatcca gtctattaat    4380
tgttgccggg aagctagagt aagtagttcg ccagttaata gtttgcgcaa cgttgttgcc    4440
attgctacag gcatcgtggt gtcacgctcg tcgtttggta tggcttcatt cagctccggt    4500
tcccaacgat caaggcgagt tacatgatcc cccatgttgt gcaaaaaagc ggttagctcc    4560
ttcggtcctc cgatcgttgt cagaagtaag ttggccgcag tgttatcact catggttatg    4620
gcagcactgc ataattctct tactgtcatg ccatccgtaa gatgcttttc tgtgactggt    4680
gagtactcaa ccaagtcatt ctgagaatag tgtatgcggc gaccgagttg ctcttgcccg    4740
gcgtcaatac gggataatac cgcgccacat agcagaactt taaaagtgct catcattgga    4800
aaacgttctt cggggcgaaa actctcaagg atcttaccgc tgttgagatc cagttcgatg    4860
```

```
taacccactc gtgcacccaa ctgatcttca gcatcttttta ctttcaccag cgtttctggg    4920
tgagcaaaaa caggaaggca aaatgccgca aaaagggaa taagggcgac acggaaatgt      4980
tgaatactca tactcttcct ttttcaatat tattgaagca tttatcaggg ttattgtctc     5040
atgagcggat acatatttga atgtatttag aaaaataaac aaatagggt tccgcgcaca      5100
tttccccgaa aagtgccacc taaattgtaa gcgttaatat tttgttaaaa ttcgcgttaa     5160
attttttgtta aatcagctca ttttttaacc aataggccga aatcggcaaa atcccttata    5220
aatcaaaaga atagaccgag atagggttga gtgttgttcc agtttggaac aagagtccac     5280
tattaaagaa cgtggactcc aacgtcaaag ggcgaaaaac cgtctatcag ggcgatggcc     5340
cactacgtga accatcaccc taatcaagtt ttttggggtc gaggtgccgt aaagcactaa     5400
atcggaaccc taaagggagc ccccgattta gagcttgacg gggaaagccg gcgaacgtgg     5460
cgagaaagga agggaagaaa gcgaaaggag cgggcgctag ggcgctggca agtgtagcgg     5520
tcacgctgcg cgtaaccacc acacccgccg cgcttaatgc gccgctacag gcgcgtccc     5580
attcgccatt caggctgcgc aactgttggg aagggcgatc ggtgcgggcc tcttcgctat     5640
tacgccagct ggcgaaaggg ggatgtgctg caaggcgatt aagttgggta acgccagggt    5700
tttcccagtc acgacgttgt aaaacgacgg ccagtgagcg cgcgtaatac gactcactat    5760
agggcgaatt ggagctccac cgcggtggcg gccgtcgatc gacgcgaaga acgatctcct    5820
cgagctgttc gcggatcagc ttgtagccct gcagtggaac caggccgacg gcccgctcct    5880
tgcggaccac ggtggctggc gcgcccaatt tgtgaaccag gtcgtttagg acctcctgcg    5940
caaagtccag tgttaggaga atgtcctcct gggaccaatt cagcatgttc tcgagcagcc    6000
atctgtcttt ggagtaaaaa cgtaatttct gctcctcgtt actgtaccgg aaaagataat    6060
ttgcctcgcc gccataata agaaggttct ttttctggtg gcctttgagc agcggggacg     6120
tttggacagc gtcgatgagg cccttgaggc gctcgtagta cttggtcgcg tcgttgtagc    6180
cggccgcggt gacgataccc acataaaggt cttttggccat tagcttgatg aggtggggta   6240
agatgggcga ctcggcatcg aaattttgc cgtcgtcgta cagtgtgatg tcaccatcga    6300
atgttatgag ctgcagcttg cgatctcgga tggttttgga atggaagaac cgcgacatct    6360
ccaacagctg ggccgtgttg aggatgagcc ggacgtcgtt gaacgagggc gccacaagcc    6420
ggcgtttgct gatggcgcgg cgctcgtcct cgatgtagaa ggccttttcc agaggcagtc    6480
tggtgaaaaa gttgccaacg ctcggaacca gctgcacgag ccgagacaat tcgggggtgc    6540
cggctttggt catttcaatg ttgtcgtcga tgaggagttc gaggtcgtgg aagatttctg    6600
cgtaacggcg ttttgcctca gagttcacca tgagatcgtc cacggcggag atgccgttgc    6660
tcttcaccgc gtacaggacg aacgcgcgtgg ccaacaggcc cttatccac tctatgaggc    6720
cgtctcgacg gtgttccttg agtgcatact ccactctgta gcgactagtc atccggaggc    6780
tgggctttct gcgctgggtg tactaattaa ttggtgccgc acctgtacgg ggtaccttgc    6840
atccttgcac cgcaactaaa ataaacccac tcgctttagc cttcgcgtaa aactcgtgaa    6900
tctggcaact gagggggttc tgcagccgca accaaacttt atcgctttga ggacgcagct    6960
ggatggtgtc atgtgaggct ctgttctctg gcgtagccta caacgtgact ttgcctaagc    7020
ggacggccct acccttagct gcctgcgcct gctaccagaa aatcactaga acagcagagg    7080
gccgatgtgg taattggtgc ggtgtcggcc agtctgtttc tccacagtgc aaatgcgggt    7140
gaaccggcca gaaagcaaat tcttatgct accgtgcagt gactccgaca tccccagttt    7200
ttgccctact tgatcacaga tggggtcagc actgtcgcta agtgcaccca gtcgtcccca    7260
```

```
cacgcgcaat ctataaatac tgccgccagt gcacggtggt gacatcaatc taaagtacaa    7320
aaacaaaagc ttgaattcgg cacgaggtca accccacgcc tttggcacaa tgaagtgggt    7380
aacctttatt tcccttcttt ttctctttag ctcggcttat tccaggggtg tgtttcgtcg    7440
agatgcacac aagagtgagg ttgctcatcg gtttaaagat ttgggagaag aaaatttcaa    7500
agccttggtg ttgattgcct ttgctcagta tcttcagcag tgtccatttg aagatcatgt    7560
aaaattagtg aatgaagtaa ctgaatttgc aaaaacatgt gttgctgatg agtcagctga    7620
aaattgtgac aaatcacttc atacccttttt tggagacaaa ttatgcacag ttgcaactct    7680
tcgtgaaacc tatggtgaaa tggctgactg ctgtgcaaaa caagaacctg agagaaatga    7740
atgcttcttg caacacaaag atgacaatcc aaatctcccc gttaaccatc accatcacca    7800
tcaccatcac ggtggcggtg gctcgggtgg cggtggatcc gaaaacctgt atttcagggg    7860
cgctagcatg cctacttcaa gttctacaaa gaaaacacag ctacaactgg aacatttact    7920
gctggattta cagatgattt tgaatggaat taataattac aagaatccca aactcaccag    7980
gatgctcaca tttaagtttt acatgcccaa gaaggccaca gaattgaaac atcttcagtg    8040
tctagaagaa gaactcaaac ctctggagga agtgctaaat ttagctcaaa gcaaaaactt    8100
tcacttaaga cccagggact taatcagcaa tatcaacgta atagttctgg aactaagggg    8160
atctgaaaca acattcatgt gtgaaatatgc tgatgagaca gcaaccattg tagaatttct    8220
gaacagatgg attaccttttt ctcagagcat catctcaaca ctgactgata tctggagcca    8280
cccgcagttc gaaaagtgac ccatcgctag aactagtgga tcttggctac tcaggctccg    8340
acctggacat gacgattcca aacttcagac tcggaactta cgaggagacc ggacttgcca    8400
gattctaagg agacgtggaa ggacataccg cttttgagaa gcgtgtttga aaatagttct    8460
ttttctggtt tatatcgttt atgaagtgat gagatgaaaa gctgaaatag cgagtatagg    8520
aaaatttaat gaaaattaaa ttaaatattt tcttaggcta ttagtcacct tcaaaatgcc    8580
ggccgcttct aagaacgttg tcatgatcga caactacgac tcgtttacct ggaacctgta    8640
cgagtacctg tgtcaggagg gagccaatgt cgaggttttc aggaacgatc agatcaccat    8700
tccggagatt gagcagctca agccggacgt tgtggtgatg ggctgcagga atta          8754
```

<210> SEQ ID NO 8
<211> LENGTH: 54
<212> TYPE: DNA
<213> ORGANISM: Artificial Sequence
<220> FEATURE:
<223> OTHER INFORMATION: TAG-d1

<400> SEQUENCE: 8

```
tttgttaacc acccgcagtt ggaaaagtga cccgggaagc ttggcactgg ccgt          54
```

<210> SEQ ID NO 9
<211> LENGTH: 45
<212> TYPE: DNA
<213> ORGANISM: Artificial Sequence
<220> FEATURE:
<223> OTHER INFORMATION: TAG-d2 primer

<400> SEQUENCE: 9

```
aaagctagcg gccgcgatat ctggagccac ccgcagttcg aaaag                    45
```

<210> SEQ ID NO 10
<211> LENGTH: 51
<212> TYPE: DNA

```
<213> ORGANISM: Artificial Sequence
<220> FEATURE:
<223> OTHER INFORMATION: TAG-u2 primer

<400> SEQUENCE: 10
gtggctagcg ccctgaaaat acaggttttc ggatccaccg ccacccgagc c        51

<210> SEQ ID NO 11
<211> LENGTH: 21
<212> TYPE: DNA
<213> ORGANISM: Artificial Sequence
<220> FEATURE:
<223> OTHER INFORMATION: HSA-F primer

<400> SEQUENCE: 11
ctcaagcttg aattcggcac g                                          21

<210> SEQ ID NO 12
<211> LENGTH: 34
<212> TYPE: DNA
<213> ORGANISM: Artificial sequence
<220> FEATURE:
<223> OTHER INFORMATION: HSA-u1 primer

<400> SEQUENCE: 12
tttgttaacg ggggagattt ggattgtcat cttt                            34

<210> SEQ ID NO 13
<211> LENGTH: 36
<212> TYPE: DNA
<213> ORGANISM: artificial sequence
<220> FEATURE:
<223> OTHER INFORMATION: HSA-u5 primer

<400> SEQUENCE: 13
tttgttaact aagcctaagg cagcttgact tgcagc                          36

<210> SEQ ID NO 14
<211> LENGTH: 29
<212> TYPE: DNA
<213> ORGANISM: artificial sequence
<220> FEATURE:
<223> OTHER INFORMATION: IL-2-F primer

<400> SEQUENCE: 14
ctagctagca tgcctacttc aagttctac                                  29

<210> SEQ ID NO 15
<211> LENGTH: 47
<212> TYPE: DNA
<213> ORGANISM: artificial sequence
<220> FEATURE:
<223> OTHER INFORMATION: IL-2-R (w/His-Tag) primer

<400> SEQUENCE: 15
gcttgatatc tcagtggtgg tggtggtggt gagtcagtgt tgagatg               47
```

INTERLEUKIN-2 EXPRESSION CONSTRUCT USING HUMAN SERIUM ALBUMIN

REFERENCE TO SEQUENCE LISTING SUBMITTED ELECTRONICALLY VIA EFS-WEB

The content of the electronically submitted sequence listing (Name: 19716-0020001_ST25.txt; Size: 33,916 bytes; and Date of Creation: Aug. 24, 2017) is incorporated by reference in its entirety.

TECHNICAL FIELD

The present invention relates to an interleukin-2 expression construct using human serum albumin and transformed yeast containing the expression construct.

BACKGROUND ART

The medical proteins or industrial enzymes useful for humans, which could only be obtained in a trace amount from the natural state in the past, could be mass-produced by the development of recombinant DNA technology. For example, E. coli cells have been most widely used as host cells for producing large amounts of such useful proteins, and useful recombinant proteins, including hormones such as insulin and β-endorphin, and immunomodulators such as interferon, have been produced by E. coli.

However, there is a limit to the production of either glycoproteins that require post-translational modification such as glycosylation to have activity, or proteins having a very large and complex structure. Furthermore, when a useful protein is expressed in yeast, an insoluble inclusion body protein is formed which lost its activity by various mechanisms without being completely is formed. Although this insoluble protein may be easily isolated in an initial stage to provide a highly pure protein in some cases, it lacks activity as the protein. For this reason, complex and costly denaturation and refolding processes are required to obtain a biologically active soluble protein from the insoluble protein. Thus, there has been increasing interest in a method for producing a large amount of a target protein as a form of secretion.

Meanwhile, interleukin-2 consists of 153 amino acids and is produced mainly by T cells expressing the surface antigen CD4. Transformed T cells, B cells, lymphocytic cancer cells, LAK cells and NK cells also secrete interleukin-2. It is known that the production of interleukin-2 is induced by mitogen- or allergen-mediated activation of T cells, and several kinds of secondary stimulations are required to maximize the production of interleukin-2, but resting cells cannot produce interleukin-2. It has been reported that interleukin-2 and its receptor are associated with many disease However, studies on the molecular characteristics of interleukin-2 and its receptor have been very limited, because they are obtained in limited amounts.

For example, many methods have been studied to increase immunity against cancer by administration of functional interleukin-2 gene, and thus studies on interleukin-2 and the demand for interleukin-2 as a therapeutic agent have continued to increase. However, technology for producing a large amount of interleukin-2 is still insufficient.

Under this background, it is necessary to develop a gene expression system for mass production of interleukin-2 using various expression systems.

DISCLOSURE

Technical Problem

An object of the present invention to provide an interleukin-2 expression construct for yeast, comprising: a methanol oxidase (MOX) promoter; a human serum albumin gene or a fragment thereof; and an interleukin-2 (IL-2) gene.

Another object of the present invention is to provide a transformant comprising the expression construction.

Still another object of the present invention is to provide a method for producing interleukin-2 using the transformant.

Technical Solution

To achieve the above objects, the present inventors have found that interleukin-2 (IL-2) is a suitable protein capable of being fused to human serum albumin (HSA) that can be easily expressed and secreted from yeast cells. Furthermore, the present inventors have induced expression of a fusion protein of human serum albumin and interleukin-2, and treated the secreted fusion protein of human serum albumin and interleukin-with tobacco etch virus (TEV) protease to recover pure interleukin-2 as a desired protein, thereby completing the present invention.

The interleukin-2 expression construct for yeast according to the present invention and a yeast comprising the same may be cultured with methanol (that is an inexpensive carbon source), and have a strong promoter that is induced by methanol, unlike an expression construct or expression system that is used in a known method for producing recombinant interleukin-2. In this regard, interleukin-2 expression construct for yeast according to the present invention and a yeast comprising the same have a significant effect on the production of a large amount of interleukin-2.

The present invention provides an interleukin-2 expression construct for yeast, comprising: a methanol oxidase (MOX) promoter; a human serum albumin gene or a fragment thereof; and an interleukin-2 (IL-2) gene. The interleukin-2 expression construct for yeast according to the present invention may be inducibly expressed by a carbon source related to methanol metabolism in a transformant, and thus makes it possible to mass production of interleukin-2 at low costs.

As used herein, the term "expression construct" means a nucleic acid molecule that comprises only the minimum elements for intracellular protein expression. Preferably, the expression construct according to the present invention comprises the above-mentioned elements as the minimum essential elements.

The expression construct of the present invention may be a recombinant vector. Preferably, it may be a vector constructed according to a recombinant vector construction method known in the art. Specifically, it may be a vector obtained by linking the methanol oxidase (MOX) promoter upstream of the full-length sequence of the human serum albumin gene or a fragment thereof, and linking the linked promoter upstream of the interleukin-2 gene. For example, a pYHSA13 (T-1) vector comprises: an MOX promoter which is the methanol inducible promoter of *Hansenula polymorpha*; an ampicillin-resistant gene which is a selectable marker for E. coli; leu which is a marker gene for *Hansenula polymorpha*; and a human serum albumin (HSA) gene which is secreted and expressed by the MOX promoter. Of the cleaved sequences of the pYHSA13 (T-1) vector, the nucleotide sequence comprising human serum albumin may be ligated into the high-copy vector pUC1.8 for E. coli to obtain a recombinant vector (pUC18-HSA), and interleukin-2 may be cloned into the recombinant vector (pUC18-HSA), thereby constructing a recombinant vector for fusion expression. FIG. 1 shows a schematic view of the pUC18-HSA recombinant vector.

In the present invention, the methanol oxidase (MOX) promoter is a promoter derived from the genomic DNA of *Hansenula polymorpha*. The MOX promoter that is used in the present invention is a strong promoter that easily controls expression, and can be integrated into multiple sites on each chromosome. Thus, an expression vector comprising the methanol oxidase (MOX) promoter is highly stable in a long-term culture process performed using a non-selective medium. Accordingly, the MOX promoter is very effectively used for expression of interleukin-2. The MOX promoter that is used in the present invention may have a nucleotide sequence of SEQ ID NO: 1. In addition, nucleotide sequences, which have properties functionally equivalent to the nucleotide sequence of SEQ ID NO: 1 and have a sequence homology of 90%, 91%, 92%, 93%, 94%, 95%, 96%, 97%, 98%, 99% or more to the nucleotide sequence of SEQ ID NO: 1, also fall within the scope of the present invention.

As used herein, the expression "human serum albumin gene or a fraament thereof" refers to either a gene encoding a molecular weight 65-kDa protein consisting of 585 amino acids, which is produced in the liver and secreted into blood, or a fragment of a gene encoding human serum albumin. The human serum albumin gene or a fragment thereof, which is used in the present invention, encodes a protein having a secretory signal sequence, and is easily secreted by itself without requiring a secretory system. Particularly, when the human serum albumin protein is used as a fusion protein with interleukin-2 in expression of interleukin-2 whose expression and secretion is not easy due to s large size or complex structure, it significantly increases the expression and secretion of interleukin-2. In the present invention, the human serum albumin gene has a nucleotide sequence of SEQ ID NO: 2. In addition, nucleotide sequences, which have properties functionally equivalent to the nucleotide sequence of SEQ ID NO: 2 and have a sequence homology of 90%, 91%, 92%, 93%, 94%, 95%, 96%, 97%, 98%, 99% or more to the nucleotide sequence of SEQ ID NO: 2, also fall within the scope of the present invention. Furthermore, the fragment of the human serum albumin gene is a portion of the human serum albumin gene that may be secreted by itself without requiring a secretory system, and may have a nucleotide sequence encoding an amino acid. sequence consisting of 100, 200, 300, 400, 500 or more amino acids counted from the N-terminus of thefull-length amino acid. sequence of human serum albumin. Preferably, the fragment of the human serum albumin gene has a nucleotide sequence of SEQ ID NO: 3.

In the present invention, interleukin-2 is a protein consisting of 153 amino acids, which is produced mainly by T cells expressing the surface antigen CD4. The interleukin-2 gene that is used in the present invention has a nucleotide sequence of SEQ ID NO: 4. In addition, nucleotide sequences, which have properties functionally equivalent to the nucleotide sequence of SEQ ID NO: 4 and have a sequence homology of 90%, 91%, 92%, 93%, 94%, 95%, 96%, 97%, 98%, 99% or more to the nucleotide sequence of SEQ ID NO: 4, also fall within the scope of the present invention.

The expression construct of the present invention is used in yeast. According to a preferred embodiment of the present invention, the yeast is a methylotrophic yeast. More preferably, the yeast is *Hansenula polymorpha, Pichia pastoris, Candia boidini, Pichia methanolica*, or *Ogataea minuta*. Even more preferably, the yeast is *Hansenula polymorpha*.

The interleukin-2 expression construct for yeast according to the present invention may further comprise, between the human serum albumin gene sequence and the interleukin-2 gene sequence, a sequence that can be cleaved by protease so as to recover only the IL-2 sequence after production of a fusion protein by the expression construct. As used herein, the term "protease" refers to an enzyme that cleaves the peptide bonds of amino acids. The protease may be, for example, serine protease, threonine protease, cysteine protease, aspartate protease, metalloprotease, glutamic acid protease, or a combination of two or more thereof. In addition, the protease may be, for example, TEV (tobacco etch virus) protease, trypsin, chymotrypsin, elastase, pepsin, enteropeptidase, or a combination of two or more thereof. Regions that can be cleaved by enzymes may vary depending on. the kind of enzyme, and are known to those skilled in the art. In the present invention, a sequence that can be cleaved by the protease is the tobacco etch virus protease site that can be cleaved by tobacco etch virus protease and that has a nucleotide sequence of SEE ID NO: 5.

The expression construct according to the present invention further comprises restriction enzyme recognition nucleotide sequences that enable a foreign protein-encoding nucleotide sequence to be cloned so as to be operably linked to the promoter sequence.

Restriction enzymes that are recognized by the restriction enzyme recognition nucleotide sequences comprised in the expression construct of the present invention are not particularly limited. Examples of the restriction enzymes include, but are not limited to, EcoRV, Nhei, NotI, SphI, XbaI. and the like. Preferably, the restriction enzymes may be EcoRV and NheI.

The expression construct of the present invention comprises a transcription terminator sequence. For example, the expression construct comprises a polyadenylation sequence. For example, the expression construct comprises a bovine growth hormone terminator, an SV40-derived polyadenylation sequence, β-globin polyA, HSV TK polyA or MOX terminator, but is not limited thereto.

In addition, the expression construct according to the present invention may comprise, as a selectable marker, an antibiotic-resistant gene that is generally used in the art. For example, the expression construct comprises a gene resistant to ampicillin, gentamicin, carbenicillin, chloramphenicol, streptomycin, kanamycin, geneticin (G418), neomycin or tetracycline.

The expression construct according to the present invention may further comprise, in addition to the above-described elements, functional connections operably linked to nucleic acid expression regulatory sequence capable of regulating the transcription and/or translation of the nucleic acid sequence.

The expression construct according to the present invention is preferably an expression construct shown in FIG. 3(*a*) or 3(*b*). More preferably, the expression construct is an expression construct shown in FIG. 3(*a*). According to one embodiment of the present invention, the expression construct has a nucleotide sequence of SEQ ID NO: 6 or SEQ ID NO: 7.

The present invention also provides transformed yeast comprising the interleukin-2 expression construct for yeast. The yeast according to the present invention is preferably transformed yeast which is methylotrophic yeast For example, the transformed yeast may be transformed *Han-*

*senula polymorpha, Pichia pectoris, Candle boidini, Pichia methanolica,* or *Ogataea minute*. More preferably, the yeast according to the present invention is *Hansenula polymorpha*. Most preferably, the transformed yeast is transformed *Hansenula polymorpha* DL1-L deposited under accession number KCTC 18329P on Oct. 1, 2014 at the Korean Collection for Type Cultures, and converted on Dec. 14, 2018 to a deposit under the Budapest Treaty at the Korean Collection for Type Cultures as accession number KCTC 13777BP.

In the present invention, a method of transforming yeast cells with the expression construct may be performed using a method of transforming eukaryotic cells with a vector as known in the art. Examples of the method for transformation include microinjection, calcium phosphate precipitation, electroporation, liposome-mediated transfection, DEAE-dextran treatment, gene bombardment, and acetic-lithium DMSO methods.

The present invention also provides a method for producing interleukin-2 using yeast, the method comprising the steps of:

(a) cloning an interleukin-2 expression construct for yeast, comprising: a methanol oxidase (MOX) promoter; a human serum albumin gene or a fragment thereof; and an interleukin-2 gene;

(b) transforming yeast host cells with the expression construct prepared in step (a), and culturing the transformed yeast cells to express interleukin-2; and (c) isolating the expressed interleukin-2 protein from the transformed yeast cells cultured in step (b).

Advantageous Effects

The interleukin-2 expression construct for yeast according to the present invention makes it possible to produce an expressed and secreted fusion protein of human serum albumin (HSA) and interleukin-2 at low costs, and easily separate recombinant interleukin-2 from the fusion protein. Thus, the expression construct may be effectively used to produce a large amount of recombinant interleukin-2 protein with high purity.

DESCRIPTION OF DRAWINGS

FIG. 1 shows schematic views of a pYHSA13 (T-1) vector and a pUC18-HSA vector.

FIG. 2 shows a schematic view of a PUC-HSA-IL-2 vector comprising IL-2.

FIG. 3 shows schematic views of the specific configurations of pHSAft-5-IL-2 and pHSAft-1-IL-2 vectors.

FIG. 4 shows the results of examining the expression and secretion of an HSA-IL2 fusion protein and interleukin-2 from *H. polymorpha* transformed with a pHSAft-5-IL-2 vector.

FIG. 5 shows the results of examining the expression and secretion of an HSA-IL2 fusion protein and interleukin-2 from *H. polymorpha* transformed with a pHSAft-1-IL-2 vector.

FIG. 6 shows the results of HPLC analysis of interleukin-2 produced in *H. polymorpha* transformed with a pHSAft-1-IL-2 vector.

MODE FOR INVENTION

The advantages and features of the present invention, and the way of attaining them, will become apparent with reference to the examples described below. However, the present invention is not limited to the examples disclosed below and can be embodied in a variety of different forms. Rather, these examples are provided so that this disclosure will be thorough and complete, and will fully convey the scope of the present invention to those skilled in the art. The scope of the present invention will be defined by the appended claims.

EXAMPLE 1

Construction of Human Serum Albumin and Interleukin-2 Fusion Expression Vector

To obtain a vector set for *Hansenula polymorpha*, which can express and secrete HSA-IL-2 fusion proteins, by use of two human serum albumin (HSA) gene fragments having different sizes, a pYHSA13 (T-1) vector for *H. polymorpha*, which his a His-tag attached to the C-terminus of HSA gene, and a pUC18 vector (Invitrogen) which is a high-copy vector for *E. coli*, were used. Herein, the pYHSA13 (T-1) vector comprises: a MOX promoter which is the methanol inducible promoter of *H. polymorpha*; an ampicillin-resistant gene which is a selectable marker for *E. coli*; leu which is a marker gene for *H. polymorph a*; and a HSA gene which is expressed and secreted by the MOX promoter.

The pYHSA13 (T-1) vector was cleaved with EcoRI and BamHI to obtain three vector fragments. Among the vector fragments, a 1.8-kb fragment comprising the HSA, His-tag gene from the 5'-UTR of the vector was subcloned into a pUC18 vector that is a high-copy vector for *E. coli*, thereby constructing a pUC18-HSA vector. Schematic views of the pYHSA13 (T-1) vector and the pUC18-HSA vector are shown in FIG. 1.

To perform a series of genetic engineering operations for introducing functional domains, long primers having a tag length of 50-mer or more were used. In the first PCR, a functional domain linker and a Strep-tag sequence were constructed using HpaI-tagged primers, and in the second PCR, a multiple cloning site and a Tee sequence were constructed using NheI-tagged primers, and the first primer tag HpaI sequence was removed. Finally, in the third PCR, a HpaI recognition sequence was made between the HSA fragment and the His-tag sequence, followed by linkage with 6xHis. The primer sequences used in the PCR are shown in Table 1 below,

TABLE 1

| Primer sequences | |
|---|---|
| Primers | Sequences |
| TAG-d1 (SEQ ID NO: 8) | TTTGTTAACCACCCGCAGTTGGAAAAGTGACCCG GGAAGCTTGGCACTGGCCGT |
| TAG-d2 (SEQ ID NO: 9) | AAAGCTAGCGGCCGCGATATCTGGAGCCACCCGC AGTTCGAAAAG |
| TAG-u2 (SEQ ID NO: 10) | GTGGCTAGCGCCCTGAAAATACAGGTTTTCGGAT CCACCGCCACCCGAGCC |
| HSA-F (SEQ ID NO: 11) | CTCAAGCTTGAATTCGGCACG |
| HSA-u1 (SEQ ID NO: 12) | TTTGTTAACGGGGGAGATTTGGATTGTCATCTTT |
| HSA-u5 (SEQ ID NO: 13) | TTTGTTAACTAAGCCTAAGGCAGCTTGACTTGCA GC |

The IL-2 gene was cloned into the pUC18-HSA vector, thereby constructing a fusion expression vector enabling a HSA/IL-2 fusion protein to be efficiently expressed and secreted. In order to enable the expressed and secreted fusion protein to be effectively separated, HSA-His tag and IL-2-Strep tag binding sites were inserted into the fusion expression vector, and a TEV protease site for recovering only the IL-2 protein after expression and secretion was attached between the HSA and IL-2 genes. A schematic view of the fusion expression vector is shown in FIG. 2.

In order to construct the HSA/IL-2 fusion expression vector enabling secretion of the IL-2 protein to be efficiently induced, each of the full-length sequence of the HSA gene and the 137-amino acid fragment sequence in front of thereof was linked upstream of the IL-2 gene, thereby constructing pHSAft-5-IL-2 and pHSAft-i-IL-2 vectors enabling HSA and IL-2 to be expressed and secreted as a fusion protein. The specific configurations of the vectors are shown in FIGS. 3(a) and 3(b), respectively. The sequences of the pHSAft-5-IL2 and pHSAft-1-IL-2 vectors are shown by SEQ ID NOs: 6 and 7, respectively. In the process of performing PCR using as a template the pUC18-HSA vector having the functional domains introduced therein, different reverse primers were used to construct two HSA fusion tag domains having different sizes. HSA cleavage sites were determined based on the three-dimensional structure of HSA, and the desired DNA fragments were obtained by PCR and cloned upstream of the functional domains. Using the same, vectors for expressing the fusion protein were constructed. The primer set used in the PCR is shown in Table 2 below.

TABLE 2

Primer sequences

| Primers | Sequences |
| --- | --- |
| IL-2-F (SEQ ID NO: 14) | CTAGCTAGCATGCCTACTTCAAGTTCTAC |
| IL-2-R (w/His-tag) (SEQ ID NO: 15) | GCTTGATATCTCAGTGGTGGTGGTGGTGG TGAGTCAGTGTTGAGATG |

EXAMPLE 2

Construction of Transformant

To perform transformation using the constructed vectors, *H. polymorpha* DL1-L precultured in YPD (2% (w/v) bacto-peptone, 1% (w/v) bacto-yeast extract, and 2% (w/v) D-glucose) liquid medium was adjusted to an initial OD600 value of 0.2 in a 500-ml baffled flask, and 50 ml of the strain was cultured at 180 rpm in a shaking incubator at 30° C. The strain was cultured for 6-7 hours until the OD600 value reached 1.0. Next, the culture was centrifuged at 4,000 rpm for 10 minutes at 4° C. The supernatant was removed, and the pellet was suspended by pipetting in 1 ml of LiAc/TE buffer (0.01 M Tris-HCl, 1 mM EDTA, 0.1 M LiAc, pH 7.5). The suspension was centrifuged at 13,000 rpm for 1 minute to obtain a precipitate. Then, the pellet was suspended again in 500 µl of LiAc/TE buffer to prepare competent cells. The cell suspension was dispensed into five tubes (100 µl for each tube), and 2 µl of the recombinant vector, 10 µl of salmon sperm DNA, and 600 µl of PEG/LiAc buffer (50% polyethylene glycol, 0.01 M Tris-HCl, 1 mM EDTA, 0.1 M LiAc, pH 7.5) were added to each of the tubes, and then carefully pipetted about 3-4 times. Each tube was allowed to stand at 30° C. for 30 minutes, and then 70 µl of DMSO was added thereto, following by slight pipetting. Next, the content in each tube was heat-treated at 42° C. for 15 minutes. Each tube was allowed to stand on ice for 3 minutes, followed by centrifugation at 13,000 rpm for 1 minute. The obtained precipitate was suspended in sterile distilled water, and the suspension was smeared on selective medium SC-Leu (0.67% yeast nitrogen base w/o amino acids, Leu-dropout supplement, 2% glucose, 2% agar) and incubated at 37° C. for 48 hours, thereby obtaining transformants.

EXAMPLE 3

Screening of Recombinant Strains

The pHSAft vector comprises the secretory signal sequence of HSA protein attached thereto to efficiently increase the secretion of IL-2 protein, and induces HSA and IL-2 to be expressed and secreted as a fusion protein. The difference between the pHSAft-1-IL2 vector comprising a 137-amino-acid fragment of HSA and the pHSAft-5-IL-2 vector comprising the full-length (608-amino-acid) region of NSA is only a difference in the length of HSA, and the two vectors were constructed so as to enable the IL-2 protein to be secreted.

Using the transformed strain *H. polymorpha* (pHSAft-1-IL-2) and *H. polymorpha* (pHSAft-5-IL-2), a screening experiment was performed. Each of the two transformants was plated on SC-Leu selective medium (0.67% yeast nitrogen base w/o amino acids, Leu-dropout supplement, 2% glucose, 2% agar) and incubated for 30 hours. Then, eight of the grown colonies for each transformant were selected and named "*H. polymorpha* (pHSAft-1-IL-2) B1-8" and polymorpha (pHSAft-5-IL-2) R1-8", respectively. A screening experiment was performed to screen strains showing the best cell growth and protein production. Each of a total of 16 strains (B1-8 and R1-8) was inoculated in YPM medium (2% (w/v) bacto-peptone, 1% (w/v) bacto-yeast extract, 3% (w/v) methanol), and incubated in a shaker [SI-300R, Lab Companion] for 30 hours under the conditions of 1% seed volume, 37° C. and 200 rpm.

Cell growth (OD600) was measured using a spectrophotometer [UV1240, SHIMADZU]. When the OD600 value exceeded 1.0, each strain was diluted properly and incubated for 30 hours, followed by measurement of the final OD value of each strain, thereby determining the degree of culture of each strain.

In order to quantify the amount of protein produced by each recombinant strain, the culture was cooled on ice, and then 2% sodium deoxycholate (Na-DOC) was added thereto to a final concentration of 0.02% and concentrated. 50% trichloroacetic acid (TCA) was mixed thereto to a final concentration of 7.5%, and then the sample was allowed to stand on ice for 2 hours. Next, the cooled sample was centrifuged in Centrifuge Combi-514R at 4,000 rpm for 30 minutes at 4° C., after which the supernatant was removed, and 2 ml of tetrahydrofuran (THF) was added to the precipitate. Next, the suspension was centrifuged at 4,000 rpm for 30 minutes at 4° C., after which the supernatant was removed, and tetrahydrofuran (THF)-added precipitate was removed again in the bath sonication (Powersonic 520, Hwashin Tech, Korea). The sample having the same volume as ESA standard solution 50 was prepared in a micro tube, and Brilliant Blue G-250 950 was added thereto, after which the sample was incubated at room temperature for 5 minutes, followed by measurement of the OD at 595 nm.

The results of the measurement are shown in Tables 3 and 4 below.

TABLE 3

Growth and protein growth of *H. polymorpha* (pHSAft-1-IL-2) strain (* average values)

| Strains | Cell growth* (OD) | Total proteins* (µg/ml) |
|---------|-------------------|-------------------------|
| B1      | 5.22              | 2.09                    |
| B2      | 5.22              | 2.09                    |
| B3      | 5.33              | 2.10                    |
| B4      | 4.86              | 1.28                    |
| B5      | 3.77              | 1.19                    |
| B6      | 5.42              | 2.15                    |
| B7      | 5.40              | 2.14                    |
| B8      | 5.45              | 2.16                    |

TABLE 4

Growth and protein growth of *H. polymorpha* (pHSAft-5-IL-2) strains (* average values)

| Strains | Cell growth* (OD) | Total proteins* (µg/ml) |
|---------|-------------------|-------------------------|
| R1      | 4.29              | 1.08                    |
| R2      | 4.44              | 1.15                    |
| R3      | 4.52              | 1.16                    |
| R4      | 5.41              | 2.13                    |
| R5      | 5.34              | 2.10                    |
| R6      | 3.94              | 1.20                    |
| R7      | 5.21              | 2.09                    |

As can be seen in Table 3 above, among the eight *H. polymorpha* (pHSAft-1-IL-2) strains (B1-B8) comprising a fragment of the HSA gene, the B8 strain showed values of OD 5.45 in cell growth and 2.16 µg/ml in total protein production, suggesting that the B8 strain is the best strain.

In addition, as can be seen in Table 4 above, among the eight *H. polymorpha* (pHSAft- 5-IL-2) strains (R1-R8) comprising the full-length sequence of the HSA gene, the R4 strain showed values of OD 5.41 in cell growth and 2.13 µg/ml in total protein production, suggesting that the R4 strain is the best strain.

It was shown that cell growth and total protein production were higher in the *H. polymorpha* (pHSAft-1-IL-2) strains than in the *H. polymorpha* (pHSAft-5-IL-2) strains.

Among the *H. polymorpha* (pHSAft-1-IL-2) strains that produce recombinant interleukin-2, the B8 strain (microbial name: *Hansenula polymorpha* DL1-L) was finally selected. The selected B8 strain was deposited in the Korean Collection for Type Cultures (KCTC) at the Korean Research Institute of Bioscience and Biotechnology (KRIBB) on Oct. 1, 2014 and assigned accession number KCTC 18329P on Oct. 1, 2014 at the Korean Collection for Type Cultures, and convened on Dec. 14, 2018 to a deposit under the Budapest Treaty at the Korean Collection for Type Cultures as accession number KCTC 13777BP.

EXAMPLE 4

Examination of Secretory Expression of Protein and Separation of Fusion Protein

Cells obtained by culturing the transformant in YPD liquid medium was adjusted to an OD600 of 0.1 and transferred into an E-tube in an amount suitable for seeding into YPM liquid medium. Then, the cells were centrifuged at 13,000 rpm for 1 minute. The precipitate was added with 1 ml of sterile distilled water, suspended by pipetting, and the suspension was centrifuged at 13,000 rpm for 1 minute to obtain the precipitate. The pellet was suspended and inoculated in YPM (2% (w/v) bacto-peptone, 1% (w/v) bacto-yeast extract, 3% (w/v) methanol) liquid medium to induce protein expression.

To concentrate the expressed and secreted protein, 2% sodium deoxycholate (Na-DOC) was added to a final concentration of 0.02%. 50% trichloroacetic acid (TCA) was added to a final concentration of 7.5%, and then the sample was allowed to stand on ice for 2 hours. Then, the sample was centrifuged at 4,000 rpm (Centrifuge Combi-514R) for 30 minutes at 4° C., after which the supernatant was removed, and the precipitate was added in 2 ml of tetrahydrofuran (THF). The suspension was centrifuged at 4,000 rpm for 30 minutes at 4° C., after which the supernatant was removed, and tetrahydrofuran (THF)-added precipitate was removed again in the bath sonication (Powersonic 520, Hwashin Tech, Korea).

In order to separate the expressed and secreted fusion protein, components were collected using ProTEV Plus (Promega, USA). Next, the sample was incubated in an incubator at 30° C. for 6 hours and kept at −20° C.

The prepared protein sample was electrophoresed on SDS-PAGE gel, and the gel was transferred onto a PVDF membrane (Bio-Rad) which was then assembled with a transfer caster, filled with transfer buffer (192 mM glycine, 25 mM Tris, 20% methanol), and kept at 80 V for 1 hour. Next, the PVDF membrane was placed in blocking buffer [5% skim milk, TBST (20 mM Tris-HCl, 150mM NaCl, 0.05% Tween20)] and incubated with shaking at room temperature for about 1 hour to prevent nonspecific binding. Next, the primary antibody was added to the blocking buffer, and shaken at room temperature for about 1 hour and 30 minutes, and then washed three times with TBST buffer for 10 minutes each time. Next, secondary antibody was added to the blocking buffer, and shaken for about 1 hour, and then washed three times with TBST buffer for 10 minutes each time. Thereafter, solution A and solution B of an ECL (enhanced chemiluminescence) kit were mixed at 1:1 ratio and added to the PVDF membrane which was then incubated for 1 minute to induce color development. Then, the PVDF membrane was exposed to X-ray film to detect a signal.

The results are shown in FIGS. 4 and 5.

As shown in FIG. 4, four samples were confirmed to have the HSA-IL2 fusion protein expressed and secreted from *H. polymorpha* (strain R4) transformed with the pHSAft-5-IL-2 vector. When the four samples were treated with ProTEV, it was shown that only a 13.4-kDa band was detected (#1 to #4). In addition, a protein expressed as a fusion protein with HSA was found at 47.3 kDa (#5 to #8).

As shown in FIG. 5, in the sample confirmed to have the HSA-IL2 fusion protein expressed and secreted from *H. polymorpha* (strain B8) transformed with the pHSAft-1-IL-2 vector, expression and secretion of a HSA-IL-2 fusion protein having a size of 28 kDa was observed (FIG. 5 (*a*)). When the fusion protein was treated with ProTEV, it was shown that interleukin-2 having a size of about 14 kDa was separated from the fusion protein (FIG. 5 (*b*)).

EXAMPLE 5

Confirmation of Expression and Separation of Fusion Protein

The HSA/interleukin-2 fusion protein, produced by the *H. polymorpha* (strain B8) strain transformed with the pHSAft- 1-IL-2 vector, was separated. The separated recombinant interleukin-2 protein was analyzed by HPLC. Specifically, purified samples were filtered using a 0.45 μl syringe filter and a syringe, and then loaded onto HPLC [SIMADZU, Prominence, Japan]. Vision HT C18 HL column (5 μ, length 250 nm) was used as the HPLC column, and samples were measured for 60 minutes at a flow rate of 1.0 ml/min, a temperature of 30° C., a wavelength of 280 nm and in a ratio range of 10.

The results of the HPLC analysis are shown in FIG. 6. shown in FIG. 6, the results of HPLC analysis indicated that, after 30 minutes, the peak of recombinant interleukin-2 (FIG. 6(*b*)) appeared at the same position as that of standard interleukin-2 (FIG. 6(*a*)), suggesting that recombinant interleukin-2 was separated.

Depository Authority: Korean Research Institute of Bioscience and Biotechnology;

Accession. Number: KCTC 18329P on Oct. 1, 2014 at the Korean Collection for Type Cultures, and converted on Dec. 14, 2018 to a deposit under the Budapest Treaty at the Korean Collection for Type Cultures as accession number KCTC 13777BP;

Date of Deposition: Oct. 1, 2014.

The invention claimed is:

1. An interleukin-2 expression construct for yeast, comprising:
a methanol oxidase (MOX) promoter; a human serum albumin gene fragment having a nucleotide sequence of SEQ ID NO:3; a protease site; and an interleukin-2 (IL-2) gene.

2. The interleukin-2 expression construct of claim 1, wherein the protease site is a tobacco etch virus protease site.

3. The interleukin-2 expression construct of claim 1, wherein the methanol oxidase (MOX) promoter has a nucleotide sequence of SEQ ID NO: 1.

4. The interleukin-2 expression construct of claim 1, wherein the interleukin-2 gene has a nucleotide sequence of SEQ ID NO: 4.

5. The interleukin-2 expression construct of claim 2, wherein the tobacco etch virus protease site has a nucleotide sequence of SEQ ID NO: 5.

6. A transformed yeast comprising the interleukin-2 expression construct for yeast of claim 1.

7. The transformed yeast of claim 6, Wherein the transformed yeast is a methylotrophic yeast.

8. The transformed yeast of claim 7, wherein the methylotrophic yeast is any one selected from among *Hansenula polymorpha, Pichia pastoris, Candida Pichia methanolica,* and *Ogataea minuta*.

9. The transformed yeast of claim 8, wherein the transformed yeast is a strain deposited under accession number KCTC 13777BP.

* * * * *